United States Patent [19]

Ramirez et al.

[11] Patent Number: 5,186,857
[45] Date of Patent: Feb. 16, 1993

[54] SELF-FOAMING OIL COMPOSITIONS AND PROCESS FOR MAKING AND USING SAME

[75] Inventors: Jose E. Ramirez, Trumbull; Mohan Vishnupad, Monroe, both of Conn.

[73] Assignee: Imaginative Research Associates, Inc., Bridgeport, Conn.

[21] Appl. No.: 326,377

[22] Filed: Mar. 21, 1989

Related U.S. Application Data

[63] Continuation-in-part of Ser. No. 270,263, Nov. 14, 1988, Pat. No. 4,931,204.

[51] Int. Cl.$^5$ .................. C10M 101/00; C11D 7/50
[52] U.S. Cl. ........................... 252/167; 252/164; 252/49.5; 252/DIG. 5; 252/DIG. 13
[58] Field of Search ............ 252/DIG. 5, DIG. 13, 252/49.5, 164, 167

[56] References Cited

U.S. PATENT DOCUMENTS

| | | | |
|---|---|---|---|
| 2,176,423 | 10/1939 | Jaeger | 260/481 |
| 2,995,521 | 8/1961 | Estignard-Blvard | 252/90 |
| 3,541,581 | 11/1970 | Monson | 252/90 |
| 3,912,666 | 10/1975 | Spitzer et al. | 260/2.5 E |
| 3,941,722 | 3/1976 | Shevlin | 252/524 |
| 4,048,123 | 9/1977 | Hramchenko et al. | 252/545 |
| 4,405,489 | 9/1983 | Sisbarro | 252/315.4 |
| 4,490,355 | 12/1984 | Desai | 424/70 |
| 4,554,098 | 11/1985 | Klisch et al. | 252/547 |
| 4,606,913 | 8/1986 | Aronson et al. | 424/59 |
| 4,626,529 | 12/1986 | Grollier | 514/159 |
| 4,652,389 | 3/1987 | Moll | 252/90 |
| 4,654,213 | 3/1987 | Ramirez et al. | 424/145 |
| 4,708,813 | 11/1987 | Snyder | 252/90 |
| 4,744,979 | 4/1988 | Osipow et al. | 424/73 |
| 4,769,169 | 9/1988 | Fishlock-Lomax | 252/106 |
| 4,780,100 | 10/1988 | Moll | 8/137 |

Primary Examiner—Paul Liberman
Assistant Examiner—Erin M. Higgins
Attorney, Agent, or Firm—Perman & Green

[57] ABSTRACT

The present invention relates to liquid, lotion-like aqueous oil-in-water dispersion compositons including emulsions containing large amounts of oil or oil/wax mixtures, a volatile organic foam-producing liquid, alone or in combination with foam suppressing agents, if necessary, to and surface active agent or agents which increase the solubility of the foam-producing liquid in the oil or oil/wax mixture. The present compositions are dispersions including mixtures which do not foam or self-dispense from a non-pressurized container at temperatures from RT to 120° F., then can be poured onto a wet surface at room temperatures and spread to form a thin cleansing coating which will foam under ambient conditions to leave a residue of the oil or oil/wax mixture for cosmetic, medicinal, aesthetic, protection or other purposes.

28 Claims, No Drawings

SELF-FOAMING OIL COMPOSITIONS AND PROCESS FOR MAKING AND USING SAME

This is a continuation-in-part of our earlier co-pending U.S. application, Ser. No. 270,263, filed Nov. 14, 1988 now U.S. Pat. No. 4,931,204.

BACKGROUND OF THE INVENTION

Liquid compositions containing oils and/or soluble waxes are well known for a variety of uses, such as cosmetic lotions, medicinal lotions, furniture polishes, cleansers for tile, glass, metal, etc. Some such compositions contain soaps and/or detergents to enable them to entrap air and produce a foam or lather during use. However if high levels of oil or oil/wax mixture are added to such aqueous compositions, the foam- or lather-producing properties of the compositions are substantially reduced. Therefore aqueous liquid compositions, capable of being poured from a non-pressurized container to form a foam-producing coating, have not been available with oil or oil/wax contents greater than about 4% or 5% by weight. Such low contents are not satisfactory where the purpose of the product is to apply coatings which are high in oil or oil/wax content.

Aerosol compositions containing oil and/or oil/wax ingredients and water are also well known but such compositions must be dispensed as a foam from a pressurized container and cannot be contained as a self-foaming lotion-like liquid in a non-pressurized container. Reference is made to U.S. Pat. Nos. 2,655,480 and 3,705,855 for their disclosure of such aerosol compositions.

It is also known to provide aerosol soap and detergent compositions which dispense as a single phase gel capable of being spread over the skin as a self-foaming coating, and reference is made to U.S. Pat. Nos. 3,541,581, 4,505,489 and 4,772,427 for their disclosure of such compositions.

Finally, it is known from U.S. Pat. No. 4,726,944 to provide self-foaming or post foaming aqueous liquid detergent compositions which are capable of being poured from a non-pressurized container and rubbed into the hair as a post-foaming shampoo. Such compositions contain mixtures of anionic, amphoteric and non-ionic surfactants, water-soluble gum and a volatile hydrocarbon, and foaming occurs by evaporation of the latter as the composition is applied to the hair. U.S. Pat. No. 4,744,979 relates to similar post-foaming shaving gel compositions containing an aqueous soap solution and a mixture of surface active agents comprising amine oxides and alkanolamides.

While self-foaming or post-foaming compositions of the aforementioned types intended for the cleansing of wet or dry surfaces that contain no oil or small amounts thereof are capable of being poured as clear liquid solutions from a non-pressurized container, they function well for their intended purposes only at temperatures close to room temperature, 70°–80° F. It has not been possible heretofore to produce lotion-like post-foaming compositions of these types which are detergent-based and are used for cleansing which contain large amounts of oil or oil/wax mixture for purposes of applying oil or oil/wax coatings to the skin or other wet or dry surfaces for cosmetic, medicinal, aesthetic, protective, household, automotive or other purposes. In addition, such lotion-like post-foaming compositions show a markedly increased solubility of the volatile hydrocarbon component. This property allows the non-pressurized containers to be opened at much higher temperatures, i.e., 110°–120° F.

SUMMARY OF THE INVENTION

The present invention relates to the discovery of formulations for aqueous, lotion-like compositions which contain large amounts of dispersed oil or oil/wax mixture, greater than about 5% by weight, a volatile organic foam-producing liquid and a surfactant or detergent which increases the solubility of the foam-producing liquid in the oil or oil/wax mixture, optional additional foam suppressing agents depending on the surfactant or surfactants used, the surfactant or detergent comprising the discontinuous phase of the composition, the continuous phase comprising water. This allows the presence of large amounts of the oil or oil/wax mixture without any interference with the foam-forming ability of the foam-producing liquid, whereby the composition can be poured onto a preferably wet surface and spread as a creamy lotion coating which forms a uniform fine foam within a few seconds under ambient exposure, due to the evaporation of the volatile organic foam-producing liquid, to leave an oil or oil/wax foam residue which can be rubbed over the skin or other surface for cosmetic, medicinal, aesthetic, protective, cleansing or other purposes. The presence of the oil or oil/wax on the skin during the foaming action permits the oil or oil/wax mixture, and any medicaments, emollients or other additives dissolved therein or present in the water phase to penetrate the skin and displace moisture, moisture-soluble dirt skin oils or infected matter which may be withdrawn from the skin during the foaming process, for increased effectiveness in softening and treating the skin.

The preferred compositions of the present invention are aqueous emulsions including pseudo emulsions and other aqueous dispersions which can be agitated within the container, prior to use, to form lotion-like liquids containing oil or oil/wax mixture dispersed within the continuous water phase.

DETAILED DESCRIPTION

The present compositions contain at least about 5% by weight of one or more oils, alone or in combination with one or more waxes soluble in or compatible with said oil(s), at least about 5% by weight of at least one suitable surface active agent or detergent, at least about 5% by weight of at least one volatile organic foam-producing liquid, optionally one or more foam-suppressing compounds in the amount of 2–15% by weight, and the remainder, generally less than about 60%, water.

The ingredient of the present compositions that enables the presence of large amounts of oil or oil/wax mixtures, is the surface active agent or detergent. This material preferably is present in an amount within the range of from about 5% to about 20% by weight, and preferably from 10% to about 15% by weight, to enable the incorporation of from about 5% to about 60% by weight of the oil or oil/wax mixture, preferably from 20% to about 35% by weight of said oil or oil/wax mixture.

The most critical ingredients of the present compositions from the standpoint of increasing the solubility of the volatile hydrocarbon are both the oil and surface active agent. Their combination enables the incorporation of about 15% volatile hydrocarbons, increasing their solubility to the point that the compositions of the invention can be opened to the atmosphere at temperatures much higher than room temperature.

The addition of foam-suppressing compounds also increases the solubility of the volatile hydrocarbon component. Some surfactants by their nature do not need the addition of foam-suppressing agents, while other surfactants are not suitable for commercial utilization without them.

The most preferred mild surfactants that do not need foam suppressing agents are anionic materials such as sodium methyl cocoyl taurate (sodium salts of N-methyl taurine-coconut oil amides, referred to herein as SMCT); disodium cocamido monoisopropanol amide sulfosuccinate (disodium salts of sulfo-2-cocamide-1-methyl ethyl esters of butanedioic acid, referred to herein as DCMS); sodium lauryl sulfoacetate (sodium salt of sulfo-1-dodecyl ester of acetic acid, referred to herein as SLSA); dioctyl sodium sulfosuccinate (sodium salt of the diester of 2-ethylhexyl alcohol and sulfosuccinic acid, referred to herein as DSS), and amphoteric materials such as cocamidopropyl hydroxy sultaine, referred to herein as CHS, and combinations of such detergents with each other or with small amounts of other foam-boosting surfactants.

The inclusion of foam-suppressing compounds, preferably in amounts between about 3% and 7% by weight where necessary, in combination with highly foaming surfactants allows the use of a greater variety of surfactants which, per se, are not useful for the preparation of suitable commercial products. Combinations of this type can be obtained by adding alcohols, alkoxy alcohols, etc. to surfactants like sodium lauryl sulfate, referred to herein as SLS, ammonium lauryl ether sulfate, referred to herein as ALS, and many other surfactants generally of the anionic type. A similar foam-controlling effect can be obtained by blending high foaming surfactants, generally of the anionic type, with low foaming surfactants. The preferred low foaming surfactants used for this foam controlling effect are generally of the non-ionic and the amphoteric type. Typical of these are nonoxinol-9 (nonionic) and cocampho-carboxyl glycinate (amphoteric), referred to herein as CCG.

Suitable oils for use in the compositions of the present invention include all of the conventional water-insoluble liquid or semi-solid mineral (including mixtures of petroleum derived hydrocarbons containing 10 or more carbon atoms), vegetable, synthetic and animal oils, including fatty acid esters, lanolin, etc. The particular oils selected for a particular composition will depend upon its desired function and/or its ability to dissolve additives such as fragrances, waxes, medicaments, etc.

Suitable waxes include semi-solid and solid vegetable, mineral, animal and synthetic waxes, present in amounts which are soluble in the oils present to form liquid oil-/wax mixtures.

The preferred volatile organic foam-producing liquids are those having a vapor pressure from about 4 to 14 p.s.i.g. at temperatures between about 90°-100° F., most preferably hydrocarbons having 5 or 6 carbon atoms such as isopentane, pentane and hexane. The volatile organic liquid is present in an amount between about 5% and 15% by weight, preferably between 7% and 12% by weight.

The preferred foam suppressing agents are alcohols, alkoxy alcohols, low foaming surfactants and any other suitable compounds that help prevent the compositions of the invention from self-dispensing at temperatures well in excess of room temperature.

The final essential ingredient of the present compositions is water, which is present as an oil-in-water emulsion or dispersion to form the continuous phase of the self-foaming composition. Generally the water is present in an amount between about 25% and 60% by weight of the composition, most preferably between about 35% and 45% by weight.

Other ingredients generally are present in minor amounts, less than 10% by weight and usually less than about 2% by weight. Such additives should be soluble in or miscible with either the oils or oil/wax mixtures or in the water and include perfumes or fragrances, emollients, humectants, medicaments, colorants, etc.

The following examples are illustrative of several compositions within the scope of the present invention and should not be considered limitative. The compositions thereof are produced by adding the oils or oil/wax mixtures to a suitable container, adding the surface active agents or detergents thereto and homogenizing at a suitable elevated temperature until the detergents are thoroughly dispersed in the oil or oil/wax phase, water being added while homogenizing. Finally the mixture is cooled to room temperature or lower and the volatile organic foam-producing liquid, cooled below its boiling point, is added while the composition is stirred with a mixer. Generally any additives are initially incorporated with the oils or oil/wax mixtures in the first step.

EXAMPLE 1

| Ingredients | Wt % |
|---|---|
| Mineral Oil | 35.0 |
| DCMS | 15.0 |
| Water | 40.0 |
| Pentane | 10.0 |

EXAMPLE 2

| Ingredients | Wt % |
|---|---|
| Mineral Oil | 35.0 |
| DCMS | 13.0 |
| Sodium Lauryl Sulfate | 2.0 |
| Fragrance | 0.5 |
| Water | 39.5 |
| Isopentane | 10.0 |

EXAMPLE 3

| Ingredients | Wt % |
|---|---|
| Mineral Oil | 35.0 |
| SMCT | 15.0 |
| Water | 40.0 |
| Pentane | 10.0 |

EXAMPLE 4

| Ingredients | Wt % |
|---|---|
| Mineral Oil | 35.0 |
| DCMS | 20.0 |
| Water | 35.0 |
| Pentane | 10.0 |

EXAMPLE 5

| Ingredients | Wt % |
|---|---|
| Mineral Oil | 35.0 |
| DCMS | 5.0 |
| Water | 50.0 |
| Pentane | 10.0 |

EXAMPLE 6

| Ingredients | Wt % |
|---|---|
| Petroleum Jelly | 15.0 |
| Mineral Oil | 10.0 |
| Isopropyl Palmitate | 10.0 |
| DCMS | 12.0 |
| SLS | 3.0 |
| Water | 39.5 |
| Fragrance | 0.5 |
| Isopentane | 10.0 |

EXAMPLE 7

| Ingredients | Wt % |
|---|---|
| Mineral Oil | 35.0 |
| SLSA | 5.0 |
| Water | 50.0 |
| Isopentane | 10.0 |

EXAMPLE 8 (SHAVING PREPARATION)

| Ingredients | Wt % |
|---|---|
| Mineral Oil | 15 |
| Isopropyl Palmitate | 8 |
| Glycerine | 10 |
| DCMS | 13 |
| SLS | 2 |
| Palmitic Acid | 2 |
| Water | 40 |
| Isopentane | 10 |
| NaOH to adjust to pH 8.5 | |

EXAMPLE 9 (ANTIDUNDRUFF CLEANSER)

| Ingredient | Wt % |
|---|---|
| Mineral Oil | 35.0 |
| DCMS | 15.0 |
| Omadine MDS (MgSO$_4$ adduct) | 1.0 |
| Water | 39.0 |
| Isopentane | 10.0 |

EXAMPLE 10 (PSORIATIC SKIN CLEANSER)

| Ingredient | Wt % |
|---|---|
| Petroleum Jelly | 10.0 |
| Mineral Oil | 20.0 |
| DCMS | 15.0 |
| Coal Tar Aqueous Soln. | 5.0 |
| Water | 40.0 |
| Isopentane | 10.0 |

EXAMPLE 11 (AUTO CLEANER/POLISH)

| Ingredient | Wt % |
|---|---|
| Carnauba Wax | 17.5 |
| Mineral Oil | 17.5 |
| DCMS | 9.0 |
| SLS | 1.0 |
| Water | 45.0 |
| Isopentane | 10.0 |

EXAMPLE 12 (FABRIC CLEANER)

| Ingredient | Wt % |
|---|---|
| Deodorized Kerosene | 35.0 |
| DCMS | 15.0 |
| Water | 45.0 |
| Pentane | 5.0 |

EXAMPLE 13 (COSMETIC CLEANSER)

| Ingredient | Wt % |
|---|---|
| Lanolin | 10.0 |
| Acetulan (acetylated lanolin) | 25.0 |
| DCMS | 13.0 |
| SLS | 2.0 |
| Water | 40.0 |
| Isopentane | 10.0 |

EXAMPLE 14

| Ingredients | Wt % |
|---|---|
| DCMS | 15.0 |
| Mineral Oil | 60.0 |
| Water | 15.0 |
| Isopentane | 10.0 |

EXAMPLE 15

| Ingredients | Wt % |
|---|---|
| DCMS | 5.0 |
| Mineral Oil | 35.0 |
| Water | 50.0 |
| Isopentane | 10.0 |

EXAMPLE 16

| Ingredients | Wt % |
|---|---|
| SCT | 15.0 |
| Mineral Oil | 10.0 |
| Water | 65.0 |
| Isopentane | 10.0 |

EXAMPLE 17

| Ingredients | Wt % |
|---|---|
| DSS | 15.0 |
| Mineral Oil | 35.0 |
| Water | 40.0 |
| Isopentane | 10.0 |

EXAMPLE 18

| Ingredients | Wt % |
| --- | --- |
| DCMS | 12.0 |
| SLS | 3.0 |
| Mineral Oil | 20.0 |
| Petroleum Jelly | 12.5 |
| Polyethyleneglycol-8 Dilaurate | 2.5 |
| Water | 39.5 |
| Fragrance | 0.5 |
| Hexane | 10.0 |

EXAMPLE 19 (DEPILATORY LOTION)

| Ingredients | Wt % |
| --- | --- |
| DCMS | 15.0 |
| Mineral Oil | 35.0 |
| Water | 34.0 |
| Calcium Thioglycolate | 6.0 |
| Isopentane | 10.0 |

EXAMPLE 20

| Ingredients | Wt % |
| --- | --- |
| SLS | 15.0 |
| Mineral Oil | 30.0 |
| Water | 40.0 |
| Ethyleneglycol n-Butyl ether | 5.0 |
| Pentane | 10.0 |

EXAMPLE 21

| Ingredients | Wt % |
| --- | --- |
| SLS | 15.0 |
| Mineral Oil | 35.0 |
| Water | 32.5 |
| Ethanol | 7.5 |
| Pentane | 10.0 |

EXAMPLE 22

| Ingredients | Wt % |
| --- | --- |
| SLS | 7.5 |
| Cocampho-carboxyl glycinate (CCG) | 7.5 |
| Mineral Oil | 35.0 |
| Water | 40.0 |
| Pentane | 10.0 |

EXAMPLE 23

| Ingredients | Wt % |
| --- | --- |
| SLS | 7.5 |
| Nonoxinol-9 | 7.5 |
| Mineral Oil | 35.0 |
| Water | 40.0 |
| Pentane | 10.0 |

EXAMPLE 24

| Ingredients | Wt % |
| --- | --- |
| CHS | 15.0 |
| Mineral Oil | 35.0 |
| Water | 40.0 |
| Pentane | 10.0 |

EXAMPLE 25 (SURGICAL SCRUB)

| Ingredients | Wt % |
| --- | --- |
| CHS | 15.0 |
| Chlorhexidine gluconate | 4.0 |
| Capramide DEA | 2.0 |
| Polyquaternium-7 | 0.2 |
| Mineral Oil | 18.0 |
| Petroleum Jelly | 12.0 |
| Fragrance | 0.3 |
| Water | 38.5 |
| Pentane | 10.0 |

EXAMPLE 26 (ACNE CLEANSER)

| Ingredients | Wt % |
| --- | --- |
| DCMS | 12.0 |
| ALS | 3.0 |
| Polyquaternium-7 | 0.2 |
| Mineral Oil | 30.0 |
| Benzoyl Peroxide | 5.0 |
| Glycerine | 5.0 |
| Water | 34.5 |
| Fragrance | 0.3 |
| Pentane | 10.0 |

The following Examples 27 to 31 illustrate non-functional comparative compositions:

EXAMPLE 27

| Ingredients | Wt % |
| --- | --- |
| Sodium Lauryl Sulfate (SLS) | 15.0 |
| Mineral Oil | 35.0 |
| Water | 40.0 |
| Pentane | 10.0 |

EXAMPLE 28

| Ingredients | Wt % |
| --- | --- |
| Ammonium Lauryl Ether Sulfate (ALS) | 15.0 |
| Mineral Oil | 35.0 |
| Water | 40.0 |
| Pentane | 10.0 |

EXAMPLE 29

| Ingredients | Wt % |
| --- | --- |
| Nonoxinol-9 | 15.0 |
| Mineral Oil | 35.0 |
| Water | 40.0 |
| Pentane | 10.0 |

EXAMPLE +

| Ingredients | Wt % |
| --- | --- |
| Dimethyl-1-Naphthyl Methyl Ammonium Chloride | 15.0 |
| Mineral Oil | 35.0 |
| Water | 40.0 |
| Pentane | 10.0 |

EXAMPLE 31

| Ingredients | Wt % |
| --- | --- |
| CCG | 15.0 |
| Mineral Oil | 35.0 |
| Water | 40.0 |
| Pentane | 10.0 |

In order to establish the critical nature of the components of the present compositions we have compared examples of the preferred surfactants with other surfactants considered non-functional by themselves for the purpose of this invention. The compositions of Examples 1, 3 and 24 being compared are identical in every respect to the compositions of Examples 27, 28 and 31, respectively, except by substitution of identical amounts of total surfactant. The compositions of Example 1, 3, 7, 17, and 24 were compared with the non-functional compositions of examples 27, 28, 29, 30 and 31. Each of the compositions was placed in an individual 100 ml graduated cylinder, 10 ml of water was added to 10 g of each composition, and the cylinder was closed and shaken vigorously ten times. The initial and final volumes of the foam were recorded as 1 (0 ml increase), 3 (27 ml increase), 7 (0 ml increase), 17 (0 ml increase), 24 (24 ml increase), 27 (55 ml increase), 28 (59 ml increase), 29 (8 ml increase), 30 (5 ml increase) and 31 (28 ml increase). The preferred compositions, Examples 1, 7 and 17, showed no tendency to foam in the sealed container under agitation, establishing the solubilizing effect on the volatile organic liquid and its suppression against escape and foaming within the container, whereby the compositions have excellent post-foaming properties after being poured onto the wet skin and scrubbed for cleansing action. The compositions of Example 3 an 24 foamed somewhat but still solublized the volatile organic liquid within the oil to a sufficient extent that the composition has excellent post-foaming properties similar to those of Examples 1, 7 and 17.

The compositions of examples 1, 3, 7, 17 and 24 when opened at temperatures much higher than room temperature, e.g. from 110° to 120° F., will not self-dispense. The compositions of Examples 27 and 28 foamed excessively and self-dispensed from the container even at room temperature, although they do post-foam because the volatile liquid hydrocarbon is solublized somewhat in the oil phase but only to an unsatisfactory extent.

The compositions of Examples 29, 30 and 31 while they showed little or no tendency to foam when agitated in the sealed container, they were non-functional when poured onto the skin and spread in the same manner as the other compositions since they do not self-foam or post-foam to any useful extent.

The inclusion of foam suppressing components in combination with highly foaming surfactants allows the preparation of suitable commercial products. Preparations of this type can be obtained by adding alcohols, alkoxy alcohols, etc. to the highly foaming surfactant of Examples 27. For example, the compositions of Examples 20 and 21 show limited foam increase in the sealed container under agitation, i.e., composition 20 (23 ml increase) and composition 21 (15 ml increase). This establishes the solubilizing effect on the volatile organic liquid and its suppression against escape and foaming within the container.

A similar foam-controlling effect can be obtained by blending high foaming surfactants generally of the anionic type with low foaming surfactants generally the non-ionic and amphoteric types. Thus, in Examples 22 and 23 the surfactants of the unsatisfactory compositions of Examples 29 and 31 are modified to prepare suitable commercial products by adding the low foaming surfactants of the compositions to provide additional foam-controlling effect. The foaming values of composition 22 (23 ml increase) and compositions 23 (25 ml increase) illustrate the effect of the low foaming surfactants on compositions containing SLS which, by its chemical nature, will foam uncontrollably when used alone and will produce compositions which self-dispense at room temperature. The compositions of Examples 20, 21, 22 and 23 contain foam suppressants and demonstrate controlled foaming and will not self-dispense at temperatures from 110°-120° F. All these compositions are functional when poured onto the skin and spread in the same manner as the compositions of examples 1, 3, 7, 17 and 24 since they do foam and post-foam to a useful extent.

Therefore it will be apparent to those skilled in the art that the various classes of oils or oil/wax mixtures, specific ones of which are illustrated by the various examples set forth herein, can be incorporated in large amounts in self-foaming compositions capable of being contained within non-aerosol, non-pressurized containers, preferably small-mouth rigid containers, which compositions can be poured onto the skin or other surface and rubbed or spread in the same manner as a conventional lotion and will self-generate a copious foam on the wet skin or other wet surfaces in a few seconds time. The foaming operation results from the evaporation of the organic foam-producing liquid to leave an oily foam residue which can be rubbed into the skin or over a wooden, metallic, plastic or other surface for cleaning, medication, polishing, waxing or other purposes.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

What is claimed is:

1. Aqueous, lotion-like, oil-in-water liquid emulsion composition containing large amounts of oil or oil/wax mixture, which is capable of being contained within a non-pressurized container without self-foaming therefrom when opened at a temperature of 110° F. and up to about 120° F. and capable of being poured onto a surface at temperatures at or above room temperatures and spread as a thin layer to self-develop a copious foam, said compositions comprising an aqueous emulsion containing a dispersed oil phase comprising (a) at least about 10% by weight of the total composition of at least one oil or oil/wax mixture, (b) at least about 5% by weight of the total composition of a volatile organic foam-producing liquid which is dissolved within the oil phase and evaporates at or slightly above ambient room temperature, (c) at least about 5% by weight or the total composition of at least one surface active material which increases the solubility of said foam producing liquid in said oil or oil/wax mixture to a sufficient extent that the composition is capable of being contained within a non-pressurized container without self-foaming therefrom at temperatures up to about 120° F., said surface active material being selected from the group consisting of (i) one or more surface active agents (A) which produce the necessary solubility of said foam-producing liquid in said oil or oil/wax mixture to prevent said self-foaming, and (ii) surface active mixtures of (B) one or more surface active agents which do increase the solubility of said foam-producing liquid in said oil or oil/wax mixture but to an insufficient extent to prevent said self-foaming, and (C) one or more foam suppressing agents, said surface active mixture (ii) increasing the solubility of said foam-producing liquid in said oil or oil/wax mixture to a sufficient extent to prevent self-foaming at temperatures up to about 120° F., and the remainder comprising water as the continuous phase of said liquid emulsion composition.

2. A composition according to claim 1 comprising from about 10% to 60% by weight of said oil or oil/wax mixture, from about 5% to 20% by weight of said surface active agent, from about 5% to 15% by weight of said volatile organic liquid, 0 to 15% by weight of one or more foam-suppressing agents and from about 30% to 60% by weight of water.

3. A composition according to claim 1 comprising from about 20% to 35% by weight of said oil or oil/wax mixture, from about 10% to 15% by weight of said surface active agent, from about 7% to 12% by weight of said volatile organic liquid, 0 to 7% by weight of one or more foam-suppressing agents and from about 35% to 45% by weight of water.

4. A composition according to claim 1 in which said surface active agent (A) is selected from the group consisting of sodium methyl cocoyl taurate, disodium cocamido mono isopropanolamide sulfosuccinate, sodium lauryl sulfoacetate, dioctyl sodium sulfosuccinate and cocamidopropyl hydroxy sultaine.

5. A composition according to claim 1 in which said volatile organic liquid is one having a vapor pressure from about 4 to 14 p.s.i.g. at a temperature between 90° and 100° F.

6. A composition according to claim 5 in which said volatile organic liquid comprises pentane, isopentane or hexane.

7. A composition according to claim 1 in which said oil comprises mineral oil or a mineral oil/petroleum jelly mixture.

8. A composition according to claim 1 containing a mixture (B) and (C) of surface active agents.

9. A composition according to claim 1 further containing minor amounts of one or more oil-soluble or water-soluble additives for imparting fragrance, emollient, cosmetic, medication, humectant, disinfectant or other properties to said composition.

10. A shaving composition according to claim 9 in which said oil comprises a fatty acid ester and said additives include a humectant and sufficient alkali to render said composition alkaline.

11. An anti-dandruff shampoo composition according to claim 9 in which said additives include an anti-dandruff agent.

12. A psoriatic composition according to claim 9 in which said additives include an aqueous coal tar solution.

13. A disinfectant composition according to claim 9 in which said additives include a compatible antimicrobial agent.

14. A composition according to claim 1 in which said surface active agent (A) is selected from the group consisting of anionic and amphoteric materials which render the volatile organic liquid sufficiently soluble in the oil or oil/wax phase to prevent said self-foaming in the absence of foam-suppressing agents.

15. A composition according to claim 1 in which said surface active agent comprises a mixture of (B) a surface active agent which produces a low degree of solubility of the volatile organic liquid in the oil or oil/wax phase, and (C) a foam-suppressing agent comprising an alcohol or alcohol ether which cooperates with (B) to increase the solubility of the volatile organic liquid in the oil or oil/wax phase and prevent said self-foaming.

16. A composition according to claim 1 in which said foam suppressing agent (C) comprises a low foaming surface active agent which cooperates with (B) to produce the necessary degree of solubility of the volatile organic liquid in the oil or oil/wax phase.

17. A process for applying a thin coating of oil or oil/wax composition to a surface for cosmetic, aesthetic, protective, medication, cleansing or other purposes, which comprises producing a self-foaming, lotion-like, aqueous oil-in-water liquid emulsion containing at least about 10% by weight of oil or oil/wax mixture, at least about 5% by weight of a volatile organic foam producing liquid, and at least about 5% by weight of at least one surface active material which increases the solubility of the foam-producing liquid in the oil or oil/wax so that said liquid remains dissolved to a substantial extent within the oil or oil/wax and said composition is capable of being contained within a non-pressurized container without self-foaming therefrom when opened at a temperature of 110° F. and up to about 120° F., said surface active material being selected from the group consisting of (i) one or more surface active agents (A) which produce the necessary solubility of said foam-producing liquid in said oil or oil/wax mixture to prevent said self-foaming, and (ii) surface active mixtures of (B) one or more surface active agents which do increase the solubility of said foam-producing liquid in said oil or oil/wax mixture but to an insufficient extent to prevent said self-foaming, and (C) one or more foam-suppressing agents, said surface active mixture (ii) increasing the solubility of said foam-producing liquid in said oil or oil/wax mixtures to a sufficient extent to prevent said self-foaming, pouring said lotion-like liquid emulsion onto a surface to be treated and spreading it as a thin layer exposed to ambient conditions, whereby said composition self-develops a copious foam due to the evaporation of said volatile foam-producing liquid, which foam contains said oil or oil/wax mixture and can be rubbed into or over said surface to provide a cosmetic, aesthetic, protective, medication, cleansing or other coating thereon.

18. Process for producing an aqueous, lotion-like liquid emulsion composition containing large amounts of oil or oil/wax mixture and a foam-producing volatile organic liquid dissolved therein to a sufficient extent that said composition is capable of being contained within a non-pressurized container without self-foaming therefrom when opened at a temperature of 110° F. and up to about 120° F., and capable of being poured onto a surface at temperatures at or above room temperatures and spread as a thin layer to self-develop a copious foam, which process comprises mixing together at least about 10% by weight or the total composition of at least one oil or oil/wax mixture, at least about 5% by weight of the total composition of at least one surface active material which increases the solubility of said foam-producing volatile organic liquid in said oil or oil/wax mixture, said surface active material being selected from the group consisting of (i) one or more surface active agents (A) which produce the necessary solubility of said foam-producing liquid in said oil or oil/wax mixture to prevent said self-foaming, and (ii) surface active mixtures of (B) one or more surface active agents which do increase the solubility of said foam-producing liquid in said oil or oil/wax mixture but to an insufficient extent to prevent said self-foaming, and (C) one or more foam-supressing agents, said surface active mixture (ii) increasing the solubility of said foam-producing liquid in said oil or oil/wax mixtures to a sufficient extent to prevent said self-foaming, and water, and homogenizing said composition at elevated temperatures above room temperature to form an oil-in-water emulsion, cooling said emulsion to at least about room temperature, and finally adding at least about 5% by weight, based upon the total weight of the composition, of a said foam-producing volatile organic liquid which evaporates at or above room temperature, to form an oil-in-water liquid emulsion containing said volatile organic liquid dissolved within the emulsified oil or oil/wax phase.

19. A process according to claim 18 in which said surface active agent is selected from the group consisting of sodium methyl cocoyl taurate, disodium lauryl sulfoacetate and dioctyl sodium sulfosuccinate and cocamidopropyl hydroxy sultaine.

20. A process according to claim 18 in which said volatile organic liquid is one having a vapor pressure from about 4 to 14 p.s.i.g. at a temperature between 90° and 100° F.

21. A process according to claim 20 in which said volatile organic liquid comprises pentane, isopentane or hexane.

22. A process according to claim 18 in which said oil comprises mineral oil or a mineral oil/mineral wax mixture.

23. A process according to claim 18 in which said mixture contains a mixture of surface active agents.

24. A process according to claim 18 in which said mixture further contains minor amounts of one or more oil-soluble or water-soluble additives for imparting fragrance, emollient, cosmetic, medication, humectant, disinfectant or other properties to said composition.

25. A process according to claim 18 which comprises mixing from about 10% to 60% by weight of said oil or oil/wax mixture, from about 5% to 20% by weight of said surface active agent(s), from 0 to 15% by weight of said foam suppressing agent(s), and from about 30% to 50% by weight of water and heating to form said emulsion, cooling said emulsion and dissolving thereinto from about 5% to about 15% by weight of said volatile organic liquid.

26. A process according to claim 18 which comprises mixing from about 20% to 35% by weight of said oil or oil/wax mixture, from about 10% to 15% by weight of said surface active agent(s), from 0 to 8% by weight of said foam suppressing agent(s), and from about 35% to 45% by weight of water and heating to form said emulsion, cooling said emulsion and dissolving thereinto from about 7% to about 12% by weight of said volatile organic liquid.

27. A process according to claim 18 in which said surface active agent is selected from the group consisting of anionic and amphoteric materials which render the volatile organic liquid sufficiently soluble in the oil or oil/wax phase to prevent evaporation thereof at temperatures up to about 120° F. in the absence of foam-suppressing agents.

28. A process according to claim 18 in which said surface active agent is a high foaming surface active agent which produces a low degree of solubility of the volatile organic liquid in the oil or oil/wax phase, and a foam-suppressing agent is added to increase the solubility of the volatile organic liquid in the oil or oil/wax phase to a sufficient extent to prevent evaporation thereof at temperatures up to about 120° F.

* * * * *